United States Patent [19]

Yamaguchi et al.

[11] 4,453,009

[45] Jun. 5, 1984

[54] PROCESS FOR PRODUCING FLUOROBENZOPHENONE DERIVATIVES

[75] Inventors: Akihiro Yamaguchi, Kamakura; Keizaburo Yamaguchi, Kawasaki; Kenichi Sugimoto; Yoshimitsu Tanabe, both of Yokohama, all of Japan

[73] Assignee: Mitsui Toatsu Chemicals, Inc., Tokyo, Japan

[21] Appl. No.: 433,438

[22] Filed: Oct. 8, 1982

[51] Int. Cl.³ .............................................. C07C 49/80
[52] U.S. Cl. ..................................... 568/316; 568/323
[58] Field of Search ................................. 568/316, 323

[56] References Cited

U.S. PATENT DOCUMENTS 2,533,132  12/1950  McBee et al. ..................... 568/316

OTHER PUBLICATIONS

Pews et al., "J. Amer. Chem. Society", vol. 89, #10 (1967), p. 1162.
Dunlop et al., "J. Amer. Chem. Society", vol. 55, (1933), pp. 1665–1666.
Bradlow et al., "J. Amer. Chem. Society", vol. 69, (1947), pp. 662–663.
Colorado et al., "Chem. Abstracts", vol. 42 (1948), p. 1920i.
Eckstein et al., "Chem. Abstracts", vol. 54 (1960), p. 21005b.
Picard et al., "Chem. Abstracts", vol. 44 (1950), p. 4442.

Primary Examiner—Werren B. Lone
Attorney, Agent, or Firm—Albert L. Jeffers; John F. Hoffman

[57] ABSTRACT

4-Fluorobenzophenone derivatives of 4,4'-difluorobenzophenone are produced by effecting a halogen-fluorine exchanging reaction between the corresponding 4-halogenobenzophenone derivatives or 4,4'-dihalogenobenzophenone and an alkali fluoride.

The reaction is carried out by heating in an organic solvent. After distilling off the solvent from the reaction product mixture, the end product is isolated by extracting with a solvent. Alternatively the end product is isolated by distillation.

5 Claims, No Drawings

PROCESS FOR PRODUCING FLUOROBENZOPHENONE DERIVATIVES

BACKGROUND OF THE INVENTION

This invention relates to a process for the production of fluorobenzophenone derivatives and particularly, 4-fluorobenzophenone derivatives and 4,4'-difluorobenzophenone.

Fluorobenzophenone derivatives, for example 4,4'-difluorobenzophenone are used as materials for producing an aromatic polyketone polymer and 4-fluorobenzophenone derivatives are useful for agricultural chemicals and intermediates for dyestuffs.

For producing 4,4'-difluorobenzophenone, there have been known, for example, (1) a process of reacting fluorobenzene with carbon tetrachloride in the presence of anhydrous aluminum chloride and then hydrolyzing [J. P. Picard et al, Can. J. Research, 28B, 56 (1950); C.A., 44, 4442a (1950); Funasaka et al, Yukigoseikagaku Kyokaishi, 17, 334 (1959)], (2) a process of effecting Friedel-Crafts' reaction between p-fluorobenzoylchloride and fluorobenzene in the presence of anhydrous aluminum chloride [R. C. Iris et al, Rev. inst. Salubridad y enfermeded. trop., 8, 63 (1947); C.A., 42, 1921a (1948)], (3) a process of oxidizing 2,2'-bis(4-fluorophenyl)-1,1-dichloroethylene with chromic acid [H. L. Bradlow et al, J. Am. Chem. Soc., 69, 662 (1947)] and (4) a process of treating 4,4'-diaminodiphenylmethane with sodium nitrite in anhydrous hydrogen fluoride or in a concentrated aqueous solution of hydrogen fluoride (Japanese Patent Application Kokai No. 54-132,558).

Also, for producing 4-fluorobenzophenone derivatives there have been known, for example, (5) a process of effecting Friedel-Crafts' reaction between a substituted benzoylchloride and fluorobenzene in the presence of anhydrous aluminum chloride [R. D. Dunlop et al, J. Am. Chem. Soc., 55, 1665 (1933); K. C. Joshi et al, J. Indian Chem. Soc., 40, 42 (1963); R. G. Pews et al, J. Am. Chem. Soc., 89, 2392 (1967)] and (6) a process of reacting p-fluorobenzoylchloride with an aromatic hydrocarbon in the presence of anhydrous aluminum chloride [Z. Eckstein et al, Bull. acad. polon. sci., Ser. sci., chim., geol. et geograph., 7, 803 (1959); Chem. Abstr. 54, 21005b (1960)].

However, in case of the processes (1) and (2) fluorobenzene is an expensive material and anhydrous aluminum chloride of more than equimol relative to fluorobenzene is required. Also, the separation of the catalyst is too complicated to reuse it and further, apparatus of anticorrosion are required.

In case of the process (3) fluorobenzene is used as a starting material and a large amount of glacial acetic acid is necessary. Also, since an excess of anhydrous chromic acid is used, a load for treating waste fluid generated to non-pollution becomes heavy.

In case of the process (4) the starting materials are of relatively low costs, while since a large excess of anhydrous and concentrated hydrogen fluoride is used, the recovery of hydrogen fluoride is necessary.

Further, the apparatus for production made of specific materials such as a reaction and recovery vessel of anti-corrosion are required and also, the toxicity of hydrogen fluoride should be taken into consideration.

In case of the processes (5) and (6) fluorobenzene and p-fluorobenzoylchloride are expensive industrially and anhydrous aluminum chloride of more than equimol is necessary. The separation of the catalyst is too complicated to reuse it and also, the load for treating waste fluid generated is heavy. Therefore, conducting these processes in a commercial scale is confronted with various difficulties.

SUMMARY OF THE INVENTION

An object of this invention is to provide a process for producing fluorobenzophenone derivatives or 4,4'-difluorobenzophenone conveniently in a commercial scale starting from the corresponding 4-halogenobenzophenone derivatives or 4,4'-dihalogenobenzophenone.

In accordance with this invention there is provided a process for the production of 4-fluorobenzophenone derivatives or 4,4'-difluorobenzophenone which comprises effecting a halogen-fluorine exchanging reaction between a 4-halogenobenzophenone derivative of Formula I,

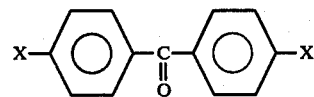

wherein X is chlorine, bromine or iodine atom, R is hydrogen, an alkyl group, an aralkyl group, a cycloalkyl group, an aryl group, an alkoxyl group, an aryloxyl group, an alkylthio group, a carboalkoxyl group, an acetyl group, a trifluoromethyl group, a nitro group or a halogen atom provided that the halogen is substituted on other positions than the 4'-position and n is an integer of 1-5 and when n is 2 or more, R may be the same or different or 4,4'-dihalogenobenzophenone of Formula II,

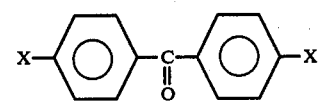

wherein X is a chlorine, bromine or iodine atom and an alkali fluoride.

DETAILED DESCRIPTION OF THE INVENTION

According to this invention, the corresponding 4-fluorobenzophenone derivatives or 4,4'-difluorobenzophenone are produced with a high yield by heating the 4-halogenobenzophenone derivative of Formula I or 4,4'-dihalogenobenzophenone of Formula II and an alkali fluoride in an organic solvent. After distilling off the solvent from the reaction product mixture, the end product is isolated easily by extracting with a solvent. Alternatively, the end product is isolated by distillation. Therefore the process of this invention is quite advantageous industrially.

The 4-halogenobenzophenone derivatives of Formula I which may be used in this invention are, for example, 4-halogenobenzophenone, 4-halogeno-3'-methylbenzophenone, 4-halogeno-4'-methylbenzophenone, 4-halogeno-4'-ethylbenzophenone, 4-halogeno-4'-n-butylbenzophenone, 4-halogeno-2',4'-dimethylbenzophenone, 4-halogeno-2',5'-dimethylbenzophenone, 4-halogeno-4'-phenylbenzophenone, 4-halogeno-4'-methoxybenzophenone, 4-halogeno-4'-ethoxybenzophenone, 4-halogeno-4'-phenoxybenzophenone, 4- halogeno-4'-methylthiobenzophenone, 4-halogeno-3'-carbomethoxybenzophenone, 4-halogeno-3'-acetylbenzophenone, 4-halogeno-3'-trifluoromethylbenzophenone, 4-halogeno-3'-nitrobenzophenone, 4-halogeno-4'-nitrobenzophenone, 2-chloro-4'-halogenobenzophenone, 2-bromo-4'-halogenobenzophenone, 3-chloro-4'-halogenobenzophenone, 4-halogeno-3',5'-dichlorobenzophenone, or the 4,4'-dihalogenobenzophenone of Formula II which may be used in this invention are 4,4'-dichlorobenzophenone, 4,4'-dichlorobenzophenone, 4,4'-dibromobenzophenone and 4,4'-diiodobenzophenone.

These 4-halogenobenzophenone derivatives of Formula I may be prepared by effecting Friedel-Crafts' reaction between p-chloro-, p-bromo- or p-iodo-benzoyl chloride and an aromatic hydrocarbon which are both available easily in a commercial scale or between a substituted benzoylchloride and chlorobenzene, bromobenzene or iodobenzene in the presence of an anhydrous ferric chloride catalyst.

The alkali fluorides which may be used in this invention are, for example, cesium fluoride, rubidium fluoride, potassium fluoride, sodium fluoride and lithium fluoride. Taking the yield of end product into consideration, cesium fluoride, rubidium fluoride and potassium fluoride are preferred. These may be used in mixture of two or more. The amount of the alkali fluoride for attaining the halogenfluorine exchanging reaction is not particularly limited, though a small excess over the stoichiometrical amount is preferred. The amount may be decided according to the yield and economy.

The organic solvent used in this invention is, for example, a sulphur-containing polar solvent e.g. dimethyl sulfoxide, dimethyl sulfone, diphenyl sulfoxide, diphenyl sulfone, tetrahydrothiophene-1,1-dioxide (sulfolane) and a nitrogen-containing polar solvent e.g. N,N-dimethylformamide, N,N-dimethylacetamide, N-methylpyrrolidone, 1,3-dimethyl-2-imidazolidinone (DMI) and hexamethylphosphoric acid triamide (HMPA) and other non-proton polar solvents.

The reaction temperature is, in general, between 100° and 350° C. The progress of the reaction is traced by a gas chromatography or thin layer chromatography and the end of the reaction is when most of the starting materials has disappeared.

The process of this invention is carried out by heating the 4-halogenobenzophenone derivatives of Formula I or 4,4'-dihalogenobenzophenone of Formula II and alkali fluoride in the organic solvent under stirring. In this case, an interlayer moving catalyst such as a large ring polyether (crown ether), quaternary ammonium salts and quaternary phosphonium salts may be added to stabilize an alkali metal cation.

According to a preferred embodiment of this invention, a small amount of benzene is added to the organic solvent containing the 4-halogenobenzophenone derivatives of Formula I or 4,4'-dihalogenobenzophenone of Formula II and alkali fluoride and heated.

Water in the reaction system is removed in the form of an azeotropic mixture with benzene and thereafter, heating is continued at indicated temperatures under stirring, which is effected, preferably under nitrogen atmosphere to prevent the solvent from decomposing.

After indicated reaction time, the resulting products are cooled and the end compound is extracted by an organic solvent.

Examples of the solvent for extraction include alcohols such as methanol, ethanol and isopropanol, halogenated hydrocarbons such as 1,2-dichloroethane, chloroform and carbon tetrachloride and benzenes such as benzene and toluene.

Alternatively, after completion of the reaction the solvent is distilled off under reduced pressure and then, the residues are subject to extraction with the above extraction solvent to isolate the end product. Also, the end product is isolated directly with the distillation under reduced pressure. If necessary, a product of high purity can be obtained from a conventional solvent recrystallization.

As mentioned above, the corresponding 4-fluorobenzophenone derivatives having only a halogen substituent on 4-position exchanged for fluorine can be obtained starting from 4-halogenobenzophenone derivatives of Formula I and the corresponding 4,4'-difluorobenzophenone having both halogen atoms on 4- and 4'-positions exchanged for fluorine can be obtained starting from 4,4'-dihalogenobenzophenone of Formula II.

This invention will be illustrated by the following non-limitative examples.

EXAMPLE 1

To a mixture of 10.1 g (0.04 mols) of 4,4'-dichlorobenzophenone, 9.3 g (0.16 mols) of potassium fluoride and 20 g of dimethyl sulfone were 5 ml of benzene added. Water in the reaction system was removed together with benzene by azeotropy. The reaction was carried out under nitrogen atmosphere at temperatures of 230°-240° C. while stirring for 45 hours.

After cooling, the reaction product was extracted under heating twice with 15 ml of isopropanol. When the extracts together were placed to cool, 7.0 g of 4,4'-difluorobenzophenone was obtained.

Yield 80%, Melting point 106°-107° C.

Pure product was obtained from recrystallisation with a methanol/water (80/20) mixture. Melting point 106°-107° C.

| Elementary Analysis | C (%) | H (%) | F (%) |
|---|---|---|---|
| Calculated | 71.5 | 3.70 | 17.4 |
| Found | 71.2 | 3.50 | 17.2 |

EXAMPLE 2

To a mixture of 10.1 g (0.04 mols) of 4,4'-dichlorobenzophenone, 9.3 g (0.16 mols) of potassium fluoride and 20 g of dimethyl sulfone were 5 ml of benzene added and water in the reaction system was removed together with benzene by azeotropy. 0.5 g of Dibenzo-18-crown-6-ether were added thereto and the reaction was carried out under nitrogen atmosphere at temperatures of 230°-240° C. while stirring for 30 hours. The post-treatment is effected in the same manner as in Example 1. 7.0 g of 4,4'-difluorobenzophenone were obtained.

Yield 80%, M.P. 106°-107° C.

EXAMPLE 3

Using 13.6 g (0.04 mols) of 4,4'-dibromobenzophenone, 9.3 g (0.16 mols) of potassium fluoride and 20 g of dimethyl sulfone, 6.8 g of 4,4'-difluorobenzophenone were obtained in the same procedure as in Example 1.

Yield 78%, M.P. 106°-107° C.

EXAMPLE 4

To a mixture of 10.1 g (0.04 mols) of 4,4'-dichlorobenzophenone, 7.0 g (0.12 mols) of potassium fluoride and 25 g of sulfolane were 5 ml of benzene added and water in the reaction system was removed together with benzene by azeotropy.

The reaction was carried out under nitrogen atmosphere at temperatures of 273°–277° C. while stirring for ten hours. After cooling the sulfolane was distilled off under reduced pressure. The residues were extracted under heating twice with 20 ml of isopropanol. When the extracts together were placed to cool, 5.7 g of 4,4'-difluorobenzophenone were obtained.

Yield 65%, M.P. 106°–107° C.

EXAMPLE 5

To a mixture of 10.1 g (0.04 mols) of 4,4'-dichlorobenzophenone, 15.2 g (0.1 mol) of cesium fluoride and 25 g of sulfolane were 5 ml of benzene added and water in the reaction system was removed together with benzene by azeotropy.

The reaction was carried out under nitrogen atmosphere at temperatures of 200°–210° C. while stirring for ten hours. After cooling the post-treatment is effected in the same manner as in Example 4 and thus, 7.4 g of 4,4'-difluorobenzophenone were obtained.

Yield 85%, M.P. 106°–107° C.

EXAMPLE 6

To a mixture of 20.2 g (0.08 mols) of 4,4'-dichlorobenzophenone, 30.4 g (0.2 mols) of cesium fluoride and 50 g of N-methylpyrrolidone were 10 ml of benzene added and water in the reaction system was removed together with benzene by azeotropy.

The reaction was carried out under nitrogen atmosphere at temperatures of 200°–202° C. while stirring for 20 hours. After cooling the N-methylpyrrolidone was distilled off under reduced pressure. 12 g of 4,4'-Difluorobenzophenone were obtained by distillation under reduced pressure.

Yield 70%, M.P. 105°–106° C.

Boiling Point 150°–155° C./12 mmHg.

Pure product was obtained from recrystallization with isopropanol.

M.P. 106°–107° C.

EXAMPLE 7

To a mixture of 10.1 g (0.04 mols) of 2,4'-dichlorobenzophenone, 4.6 g (0.08 mols) of potassium fluoride and 20 g of dimethyl sulfone were 5 ml of benzene added and water in the reaction system was removed together with benzene by azeotropy.

The reaction was carried out under nitrogen atmosphere at temperatures of 230°–240° C. while stirring for 11 hours. After cooling the reaction product was extracted under heating twice with 20 ml of isopropanol. The extracts together were placed to cool and thus, 7.5 g of 2-chloro-4'-fluorobenzophenone were obtained.

Yield 80%, M.P. 60°–61° C.

Pure product was obtained from recrystallization with isopropanol.

M.P. 60°–61° C.

EXAMPLE 8–13

Using 0.04 mols of 4-chlorobenzophenone derivatives, the reaction was carried out in the same procedure as in Example 7 to obtain the corresponding 4-fluorobenzophenone derivatives. The results obtained are set forth in Table 1.

TABLE 1

| Ex. No. | 4-Fluorobenzophenone derivatives | Yield (%) | M.P. (°C.) |
|---|---|---|---|
| 8 | 4-Fluorobenzophenone | 86 | 49–50 |
| 9 | 4-Fluoro-3'-methylbenzophenone | 81 | 97–98 |
| 10 | 4-Fluoro-4'-n-butylbenzophenone | 78 | 75–76 |
| 11 | 4-Fluoro-4'-phenylbenzophenone | 80 | 148–149 |
| 12 | 4-Fluoro-4'-ethoxybenzophenone | 72 | 87–88 |
| 13 | 4-Fluoro-3'-trifluoromethyl-benzophenone | 82 | 100–101 |

EXAMPLE 14

To a mixture of 12.2 g (0.05 mols) of 4-chloro-2',4'-dimethylbenzophenone, 12.1 g (0.08 mols) of cesium fluoride and 20 g of N-methylpyrrolidone were 5 ml of benzene added and water in the reaction system was removed together with benzene by azeotropy. The reaction was carried out under nitrogen atmosphere under reflux by heating while stirring for 15 hours. After cooling, the reaction product obtained was poured into 100 ml of water and then, extracted with 50 ml of diethyl ether and further with 50 ml of ether. The extracts together were dried and distilled and thus, 8.9 g of 4-fluoro-2',4'-dimethylbenzophenone were obtained.

Yield 78%, B.P. 151°–152° C./10 mmHg.

EXAMPLE 15

To a mixture of 14.4 g (0.05 mols) of 4-bromo-2',5'-dimethylbenzophenone, 5.5 g (0.095 mols) of potassium fluoride, 0.06 g (0.005 mols) of cesium fluoride and 20 g of sulfolane were 5 ml of benzene added and water in the reaction system was removed together with benzene by azeotropy.

The reaction was carried out under nitrogen atmosphere at temperatures of 245°–250° C. while stirring for 15 hours. After cooling, the reaction products were poured into 100 ml of water and then, extracted with 50 ml of diethyl ether and further with 50 ml of ether. The extracts together were dried and distilled and thus, 7.8 g of 4-fluoro-2',5'-dimethylbenzophenone were obtained.

Yield 69%, B.P. 164°–166° C./10 mmHg.

While this invention has been described as having preferred embodiments, it will be understood that it is capable of further modifications. This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. A process for producing 4-fluorobenzophenone derivatives or 4,4'-difluorobenzophenone which comprises reacting 4-halogenobenzophenone derivatives of Formula I,

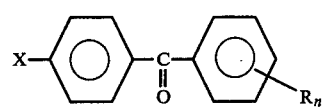

I wherein X is chlorine, bromine, or iodine atom, R is hydrogen, an alkyl group, an aralkyl group, a cycloalkyl group, an aryl group, an alkoxyl group, an aryloxyl group, an alkylthio group, a carboalkoxyl group, an acetyl group, a trifluoromethyl group, a nitro group or halogen atom provided that the halogen is substituted on other positions than 4'-position, n is an integer of 1–5 and when n is 2 or more, R is the same or different or 4,4'-dihalogenobenzophenone of Formula II

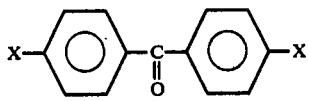

wherein X is a chlorine, bromine or iodine atom and an alkali fluoride selected from the group consisting of lithium fluoride, potassium fluoride, sodium fluoride, rubidium fluoride and cesium fluoride.

2. The process of claim 1 wherein said halogen-fluorine exchanging reaction is carried out in an organic solvent at temperatures of 100°–350° C.

3. The process of claim 1 wherein said halogen-fluorine exchanging reaction is carried out in the presence of an interlayer moving catalyst.

4. A process for producing 4-fluorobenzophenone derivatives or 4,4'-difluorobenzophenone which comprises reacting 4-halogenobenzophenone derivatives of Formula I,

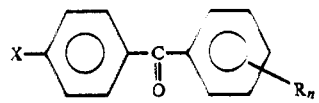

wherein X is chlorine, bromine, or iodine atom, R is hydrogen, an alkyl group, an aralkyl group, a cycloalkyl group, an aryl group, an alkoxyl group, an aryloxyl group, an alkylthio group, a carboalkoxyl group, an acetyl group, a trifluoromethyl group, a nitro group, or halogen atom provided that the halogen is substituted on other positions than the 4'-positions, n is an integer of 1–5, and when n is 2 or more, R is the same or different or 4,4'-dihalogenobenzophenone of Formula II,

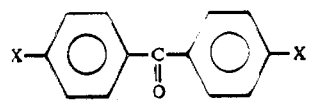

wherein X is a chlorine, bromine, or iodine atom, and an alkali flouride in an organic solvent at temperatures of about 100° C. to about 350° C., and wherein the alkali flouride is selected from the group consisting of lithium fluoride, potassium fluoride, sodium fluoride, rubidium fluoride, and cesium fluoride.

5. The process of claim 4 wherein said halogen-fluorine exchanging reaction is carried out in the presence of an interlayer moving catalyst.

* * * * *

UNITED STATES PATENT AND TRADEMARK OFFICE
CERTIFICATE OF CORRECTION

PATENT NO. : 4,453,009
DATED : June 5, 1984
INVENTOR(S) : Akihiro Yamaguchi et al.

It is certified that error appears in the above—identified patent and that said Letters Patent is hereby corrected as shown below:

Col. 2, line 7, before "fluorobenzophenone" put --4- --.
Col. 2, between lines 20-25 the correct structural formula is:

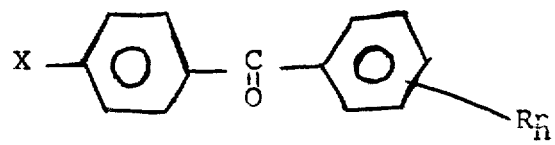

In Abstract, line 1, delete "of" and insert --or--.

Signed and Sealed this

Fourth Day of December 1984

[SEAL]

Attest:

GERALD J. MOSSINGHOFF

Attesting Officer          Commissioner of Patents and Trademarks